(12) United States Patent
Scatterday

(10) Patent No.: US 9,010,335 B1
(45) Date of Patent: Apr. 21, 2015

(54) MECHANISMS FOR VAPORIZING DEVICES

(71) Applicant: NJOY, Inc., Scottsdale, AZ (US)

(72) Inventor: Mark Scatterday, Scottsdale, AZ (US)

(73) Assignee: NJOY, Inc., Scottsdale, AZ (US)

( * ) Notice: Subject to any disclaimer, the term of this patent is extended or adjusted under 35 U.S.C. 154(b) by 0 days.

(21) Appl. No.: 14/276,547

(22) Filed: May 13, 2014

(51) Int. Cl.
*A24F 47/00* (2006.01)
*A61M 15/06* (2006.01)
*A61M 15/00* (2006.01)

(52) U.S. Cl.
CPC .............. *A24F 47/008* (2013.01); *A61M 15/06* (2013.01); *A61M 15/0001* (2014.02)

(58) Field of Classification Search
USPC ................. 128/200.14–207.29; 392/286–406
See application file for complete search history.

(56) References Cited

U.S. PATENT DOCUMENTS

| | | | |
|---|---|---|---|
| 374,584 A | 12/1887 | Cook |
| 576,653 A | 2/1897 | Bowlby |
| 595,070 A | 12/1897 | Oldenbusch |
| 799,844 A | 9/1905 | Fuller |
| 969,076 A | 8/1910 | Pender |
| 1,067,531 A | 7/1913 | MacGregor |
| 1,163,183 A | 12/1915 | Stoll |
| 1,299,162 A | 4/1919 | Fisher |
| 1,505,748 A | 3/1924 | Tamis |
| 1,552,877 A | 9/1925 | Phillipps et al. |
| 1,632,335 A | 6/1927 | Hiering |
| 1,706,244 A | 3/1929 | Meyerson |
| 1,845,340 A | 2/1932 | Ritz |
| 1,972,118 A | 9/1934 | McDill |
| 1,998,683 A | 4/1935 | Montgomery |
| 2,031,363 A | 2/1936 | Erikson |
| 2,039,559 A | 5/1936 | Segal |
| 2,327,120 A | 11/1940 | McCoon |
| 2,231,909 A | 2/1941 | Hempel |
| 2,460,427 A | 2/1949 | Musselman et al. |
| 2,483,304 A | 9/1949 | Vogel |
| 2,502,561 A | 4/1950 | Ebert |
| 2,765,949 A | 10/1956 | Hillman |
| 2,897,958 A | 8/1959 | Tarleton |
| 3,146,937 A | 9/1964 | Vesak |
| 3,420,360 A | 1/1969 | Young |
| 3,567,014 A | 3/1971 | Feigelman |
| 3,861,523 A | 1/1975 | Fountain et al. |
| 3,941,300 A | 3/1976 | Troth |
| 4,207,976 A | 6/1980 | Herman |
| 4,519,319 A | 5/1985 | Howlett |
| 4,771,796 A | 9/1988 | Myer |

(Continued)

FOREIGN PATENT DOCUMENTS

| | | |
|---|---|---|
| CN | 101869356 A | 10/2010 |
| EP | 2325093 A1 | 5/2011 |

(Continued)

*Primary Examiner* — Richard Crispino
*Assistant Examiner* — Eric Yaary
(74) *Attorney, Agent, or Firm* — Bookoff McAndrews, PLLC

(57) ABSTRACT

The present disclosure generally relates to electronic vaporizing devices comprising a plurality of components, and mechanisms for locking or otherwise securing the components together. Components of the electronic vaporizing devices may include a cartridge (e.g., including a liquid for vaporization) and a battery unit (e.g., including a rechargeable battery), among other possible components. The electronic vaporizing devices may be at least partially disassembled to allow a user to replace, replenish, recharge, and/or repair the device, as needed.

19 Claims, 2 Drawing Sheets

(56) References Cited

U.S. PATENT DOCUMENTS

| | | | |
|---|---|---|---|
| 4,798,310 A | 1/1989 | Kasai et al. | |
| 4,813,536 A | 3/1989 | Willis | |
| 4,848,375 A * | 7/1989 | Patron et al. | 131/335 |
| 4,848,563 A | 7/1989 | Robbins | |
| 5,005,759 A | 4/1991 | Bouche | |
| 5,123,530 A | 6/1992 | Lee | |
| 5,269,327 A | 12/1993 | Counts et al. | |
| 5,605,226 A | 2/1997 | Hernlein | |
| 5,641,064 A | 6/1997 | Goserud | |
| 5,746,587 A | 5/1998 | Racine et al. | |
| 5,810,164 A | 9/1998 | Rennecamp | |
| 5,881,884 A | 3/1999 | Podosek | |
| 5,938,018 A | 8/1999 | Keaveney et al. | |
| 5,967,310 A | 10/1999 | Hill | |
| 5,975,415 A | 11/1999 | Zehnal | |
| 5,979,460 A | 11/1999 | Matsumura | |
| 6,269,966 B1 | 8/2001 | Pallo et al. | |
| 6,386,371 B1 | 5/2002 | Parsons | |
| 6,431,363 B1 | 8/2002 | Hacker | |
| 6,446,793 B1 | 9/2002 | Layshock | |
| 6,510,982 B2 | 1/2003 | White et al. | |
| 6,557,708 B2 | 5/2003 | Polacco | |
| 6,622,867 B2 | 9/2003 | Menceles | |
| 6,672,762 B1 | 1/2004 | Faircloth | |
| 6,726,006 B1 | 4/2004 | Funderburk et al. | |
| 7,000,775 B2 | 2/2006 | Gelardi | |
| 7,374,048 B2 | 5/2008 | Mazurek | |
| 7,546,703 B2 | 6/2009 | Johnske et al. | |
| 7,621,403 B2 | 11/2009 | Althoff et al. | |
| 7,644,823 B2 | 1/2010 | Gelardi et al. | |
| 7,815,332 B1 | 10/2010 | Smith | |
| 7,886,507 B2 | 2/2011 | McGuinness, Jr. | |
| 7,988,034 B2 | 8/2011 | Pezzoli | |
| 8,141,701 B2 | 3/2012 | Hodges | |
| 8,443,534 B2 | 5/2013 | Goodfellow et al. | |
| 8,464,867 B2 | 6/2013 | Holloway et al. | |
| 8,539,959 B1 | 9/2013 | Scatterday | |
| 8,596,460 B2 | 12/2013 | Scatterday | |
| 2001/0032795 A1 | 10/2001 | Weinstein et al. | |
| 2001/0052480 A1 | 12/2001 | Kawaguchi et al. | |
| 2002/0043554 A1 | 4/2002 | White et al. | |
| 2002/0175164 A1 | 11/2002 | Dees et al. | |
| 2003/0089377 A1 | 5/2003 | Hajaligol et al. | |
| 2004/0149624 A1 | 8/2004 | Wischusen, III et al. | |
| 2005/0061759 A1 | 3/2005 | Doucette | |
| 2005/0118545 A1 | 6/2005 | Wong | |
| 2005/0145533 A1 | 7/2005 | Seligson | |
| 2005/0172976 A1 | 8/2005 | Newman et al. | |
| 2006/0054676 A1 | 3/2006 | Wischusen, III | |
| 2006/0150991 A1 | 7/2006 | Lee | |
| 2006/0254948 A1 | 11/2006 | Herbert et al. | |
| 2006/0255105 A1 | 11/2006 | Sweet | |
| 2007/0098148 A1 | 5/2007 | Sherman | |
| 2007/0235046 A1 | 10/2007 | Gedevanishvili | |
| 2007/0267033 A1 | 11/2007 | Mishra et al. | |
| 2008/0092912 A1 | 4/2008 | Robinson et al. | |
| 2008/0276947 A1 | 11/2008 | Martzel | |
| 2009/0095311 A1 | 4/2009 | Han | |
| 2009/0267252 A1 | 10/2009 | Ikeyama | |
| 2009/0288669 A1 | 11/2009 | Hutchens | |
| 2010/0000672 A1 | 1/2010 | Fogle | |
| 2010/0031968 A1 | 2/2010 | Sheikh et al. | |
| 2010/0186757 A1 | 7/2010 | Crooks et al. | |
| 2010/0200006 A1 | 8/2010 | Robinson et al. | |
| 2010/0242974 A1 | 9/2010 | Pan | |
| 2010/0275938 A1 | 11/2010 | Roth et al. | |
| 2010/0276333 A1 | 11/2010 | Couture | |
| 2010/0307116 A1 | 12/2010 | Fisher | |
| 2011/0049226 A1 | 3/2011 | Moreau et al. | |
| 2011/0155153 A1 | 6/2011 | Thorens et al. | |
| 2011/0162667 A1 | 7/2011 | Burke et al. | |
| 2011/0168194 A1 | 7/2011 | Hon | |
| 2011/0180433 A1 | 7/2011 | Rennecamp | |
| 2011/0232654 A1 | 9/2011 | Mass | |
| 2011/0265806 A1 | 11/2011 | Alarcon et al. | |
| 2011/0277780 A1 | 11/2011 | Terry et al. | |
| 2011/0278189 A1 | 11/2011 | Terry et al. | |
| 2011/0315701 A1 | 12/2011 | Everson | |
| 2012/0060853 A1 | 3/2012 | Robinson et al. | |
| 2012/0111347 A1 | 5/2012 | Hon | |
| 2012/0204889 A1 | 8/2012 | Xiu | |
| 2012/0227753 A1 | 9/2012 | Newton | |
| 2012/0261286 A1 | 10/2012 | Holloway et al. | |
| 2012/0267383 A1 | 10/2012 | Van Rooyen | |
| 2013/0140200 A1 | 6/2013 | Scatterday | |
| 2013/0228191 A1 | 9/2013 | Newton | |
| 2013/0247924 A1 | 9/2013 | Scatterday et al. | |
| 2013/0248385 A1 | 9/2013 | Scatterday et al. | |
| 2013/0276802 A1 | 10/2013 | Scatterday | |
| 2013/0284190 A1 | 10/2013 | Scatterday et al. | |
| 2013/0284191 A1 | 10/2013 | Scatterday et al. | |
| 2014/0014124 A1 * | 1/2014 | Glasberg et al. | 131/328 |
| 2014/0182610 A1 * | 7/2014 | Liu | 131/329 |
| 2014/0196716 A1 * | 7/2014 | Liu | 128/202.21 |
| 2014/0196731 A1 | 7/2014 | Scatterday | |

FOREIGN PATENT DOCUMENTS

| | | |
|---|---|---|
| JP | 2001-165437 A | 6/2001 |
| WO | WO-2011/033396 A1 | 3/2011 |
| WO | WO-2011/117580 A2 | 9/2011 |
| WO | WO-2012/021972 A1 | 2/2012 |
| WO | WO 2013/141906 | 9/2013 |
| WO | WO 2013/141907 | 9/2013 |
| WO | WO 2013/141994 | 9/2013 |
| WO | WO 2013/141998 | 9/2013 |
| WO | WO 2013/142671 | 9/2013 |
| WO | WO 2013/142678 | 9/2013 |
| WO | WO 2014/113592 | 7/2014 |

* cited by examiner

MECHANISMS FOR VAPORIZING DEVICES

TECHNICAL FIELD

The present disclosure generally relates to devices, systems, and methods for coupling components of a vaporizing device. More particularly, embodiments of the present disclosure include mechanisms for connecting components of an electronic vaporizing device.

BACKGROUND

Electronic cigarettes and other vaporizing or vaping devices provide an alternative to traditional smoking devices that can offer many benefits to users. These devices may be intended for single-use or limited use (e.g., disposable devices), or may be designed for multiple use or extended use (e.g., rechargeable devices) by recharging or replacing various components. For example, electronic vaporizing devices often include separable components to allow a user to recharge the device as needed. Yet, current devices often do not withstand repeated assembly and disassembly, since components may not connect securely to prevent exposing internal materials, and may be too easily damaged.

BRIEF SUMMARY

The present disclosure includes a vaporizing device comprising: a first component; a second component having an outermost diameter equal to an outermost diameter of the first component, the second component being connectable to, and removable from, the first component; and at least one locking element for restricting movement between the first and second components when the first and second components are connected; wherein an end portion of the first component includes a sheath configured to slide with respect to an end portion of the second component for connecting the first component to the second component; and wherein each of the first component and second component defines a lumen, such that, when connected, the lumens are in communication with each other and with an external environment. Embodiments of the present disclosure may include one or more of the following features: the at least one locking element may include a surface feature of the first component or the second component; the at least one locking element may be configured to apply a force radially inward; the at least one locking element may include a plurality of elements coupled to an internal surface of the first component or the second component; each element of the plurality of elements may comprise a middle portion configured to flex in a radial direction; the plurality of elements may include at least two elements coupled to internal surfaces on opposite sides of the first component or the second component; the first component or the second component may include a battery, and the other of the first component or the second component may include a liquid; the plurality of elements may be rotatable with respect to the first component or the second component to which they are coupled; the end portion of the second component may include a sheath configured to slide with respect to an inner member of the first component; the vaporizing device may comprise an electronic cigarette; and/or the electronic cigarette may be rechargeable.

The present disclosure further includes a vaporizing device comprising: a first component; a second component having an outermost diameter equal to an outermost diameter of the first component, the second component being connectable to, and removable from, the first component; and a locking element coupled to the second component for restricting movement between the first and second components when the first and second components are connected; wherein an end portion of the first component includes a sheath configured to slide with respect to a sheath of an end portion of the second component for connecting the first component to the second component. Embodiments of the present disclosure may include one or more of the following features: each of the first component and second component may define a lumen, such that, when the first and second components are connected, the lumens are in communication with each other and with an external environment for passage of air through the vaporizing device; the first component and the second component may be in communication with the external environment via an inlet at a second end potion of the vaporizing device and an outlet at a first end portion of the vaporizing device; a portion of the at least one locking element may be annular in shape; the end portion of the second component may have an outer diameter less than an outer diameter of a remainder of the second component; and/or the sheath of the first component may have a wall thickness approximately equal to a difference in the outer diameter of the end portion of the second component and the remainder of the second component.

The present disclosure further includes a vaporizing device comprising: a cartridge; a battery unit connectable to, and removable from, the cartridge; and at least one locking element for restricting movement between the cartridge and the battery unit when the cartridge and the battery unit are connected; wherein an end portion of at least one of the cartridge and the battery unit includes a sheath configured to slide with respect to an end portion of the other of the cartridge and the battery unit for connecting the cartridge to the battery unit; and wherein the vaporizing device comprises an electronic cigarette. Embodiments of the present disclosure may include one or more of the following features: the vaporizing device may comprise an outlet at a distal end of the vaporizing device and an inlet at a proximal end of the vaporizing device for passage of air through the vaporizing device, the inlet and the outlet being in communication with each other and with the external environment; and/or the battery unit may include a rechargeable battery.

It is understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Figure 1:
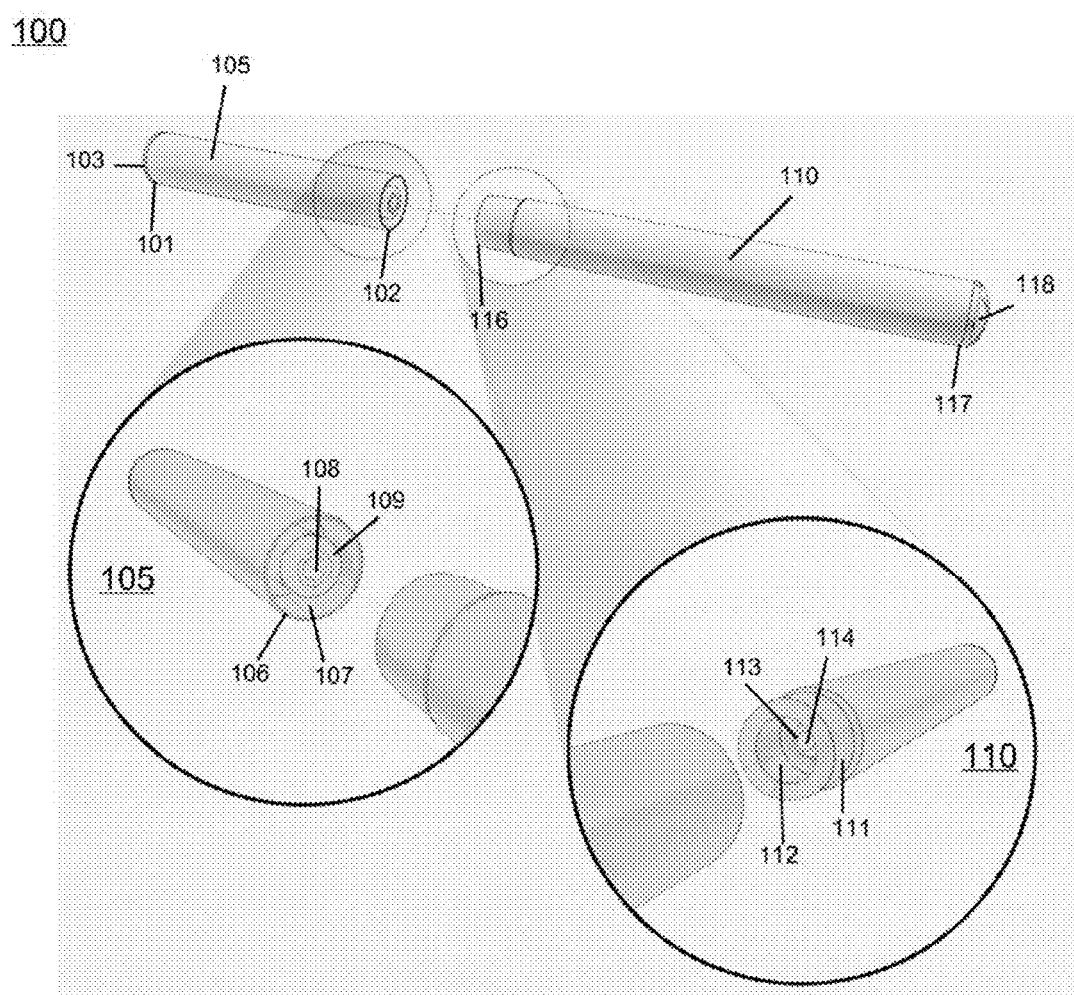
FIG. 1 shows exemplary components of a device, in accordance with one or more embodiments of the present disclosure.

Particular aspects of the present disclosure are described in greater detail below. The terms and definitions as used and clarified herein are intended to represent the meaning within the present disclosure. The patent literature referred to herein is hereby incorporated by reference. The terms and definitions provided herein control, if in conflict with terms and/or definitions incorporated by reference.

The singular forms "a," "an," and "the" include plural reference unless the context dictates otherwise.

Embodiments of the present disclosure include mechanisms for coupling two or more components of a device. The components may form part of an electronic vaporizing device such as an electronic cigarette that may be at least partially disassembled to allow a user to replace, replenish, recharge, and/or repair the device. For example, the electronic vaporizing device may comprise one or more components of a mouthpiece, a cartridge unit, a heating unit, a vaporization unit, an atomizer, a cartomizer, a clearomizer, a battery unit, a liquid tank, a light, a lighting unit, a sensor attachment, among other possible components. Embodiments of the present disclosure may include any combination of components configured for partial and/or complete disassembly and reassembly.

Various aspects of the present disclosure may be used with and/or include one or more of the features or configurations disclosed in U.S. application Ser. No. 13/729,396, filed Dec. 28, 2012, and issued as U.S. Pat. No. 8,539,959, entitled "Electronic Cigarette Configured to Simulate the Natural Burn of a Traditional Cigarette"; U.S. application Ser. No. 13/627,715, filed Sep. 26, 2012, entitled "Electronic Cigarette Configured to Simulate the Natural Burn of a Traditional Cigarette"; U.S. application Ser. No. 13/974,845, filed Aug. 23, 2013, and published as US 2013/0333712 A1, entitled "Electronic Cigarette Configured to Simulate the Natural Burn of a Traditional Cigarette"; U.S. application Ser. No. 13/741,109, filed Jan. 14, 2013, and published as US 2013/0284190 A1, entitled "Electronic Cigarette Having a Paper Label"; U.S. application Ser. No. 13/744,092, filed Jan. 17, 2013, and published as US 2013/0284191 A1, entitled "Electronic Cigarette Having a Flexible and Soft Configuration"; U.S. application Ser. No. 13/744,176, filed Jan. 17, 2013, and issued as U.S. Pat. No. 8,794,245, entitled "Aroma Pack for an Electronic Cigarette"; U.S. application Ser. No. 13/744,812, filed Jan. 18, 2013, and published as US 2013/0276802 A1, entitled "Electronic Cigarette Configured to Simulate the Filter of a Traditional Cigarette"; U.S. application Ser. No. 13/490,352, filed Jun. 6, 2012, and published as US 2013/0140200 A1, entitled "Electronic Cigarette Container and Method Therefor"; U.S. application Ser. No. 13/707,378, filed Dec. 6, 2012, and issued as U.S. Pat. No. 8,596,460, entitled "Combination Box and Display Unit"; U.S. application Ser. No. 13/495,186, filed Jun. 13, 2012, and published as US 2013/0248385, entitled "Electronic Cigarette Container"; U.S. application Ser. No. 13/954,593, filed Jul. 30, 2013, and published as US 2013/0313139, entitled "Electronic Cigarette Container"; U.S. Provisional Application No. 61/826,318, filed May 22, 2013, entitled "Compositions, Devices, and Methods for Nicotine Aerosol Delivery"; U.S. Provisional Application No. 61/856,374, filed Jul. 19, 2013, entitled "Compositions, Devices, and Methods for Nicotine Aerosol Delivery"; U.S. Provisional Application No. 61/969,650, filed Mar. 24, 2014, entitled "Compositions, Devices, and Methods for Nicotine Aerosol Delivery," U.S. Provisional Application No. 61/891,626, filed Oct. 16, 2013, entitled "Portable Vaporizer Packaging"; U.S. Provisional Application No. 61/918,480, filed Dec. 19, 2013, entitled "Vaporizing Device with Multicolor Light"; U.S. Provisional Application No. 61/906,795, filed Nov. 20, 2013, entitled "Electronic Cigarette Having Multiple Air Passages"; U.S. Provisional Application No. 61/906,803, filed Nov. 20, 2013, entitled "Leak Prevention Device for an Electronic Cigarette"; U.S. Provisional Application No. 61/906,810, filed Nov. 20, 2013, entitled "Packaging Assembly"; U.S. Provisional Application No. 61/907,002, filed Nov. 21, 2013, entitled "Electronic Cigarette and Method of Assembly Therefor"; U.S. Provisional Application No. 61/907,003, filed Nov. 21, 2013, entitled "Flexible and Stretchable Electronics for an Electronic Cigarette"; U.S. Provisional Application No. 61/847,364, filed Jul. 17, 2013, entitled "Wireless Communication System for an Electronic Cigarette"; U.S. Provisional Application No. 61/970,587, filed Mar. 26, 2014, entitled "Vaporizing Devices Comprising a Wick and Methods of Use Thereof"; U.S. Provisional Application No. 61/968,855, filed Mar. 31, 2014, entitled "Vaporizing Devices Comprising a Core and Methods of Use Thereof"; U.S. Provisional Application No. 61/971,340, filed Mar. 27, 2014, entitled "Devices and Methods for Extending Battery Power"; and/or U.S. Provisional Application No. 61/938,451, filed Feb. 11, 2014, entitled "Electronic Cigarette with Carbonaceous Material"; the disclosures of each of which are incorporated by reference herein in their entireties.

FIG. 1 shows an exemplary electronic cigarette 100, including a cartridge 105 and a battery unit 110. The cartridge 105 may have a first end portion 101 for placement in the mouth during use, e.g., the first end portion 101 is coupled to a mouthpiece 103 or filter having an outlet to allow a user to inhale vapor. The second end portion 102 of the cartridge 105 may be configured to connect to the battery unit 110 (or other component(s) of the electronic cigarette 100), as discussed below. Similarly, the battery unit 110 may have a first end portion 116 configured to connect to the cartridge 105 (or other component of the electronic cigarette 100), and a second end portion 117. The second end portion 117 of the battery unit 110 may include an inlet for the passage of air, and may be connected to other components of the electronic cigarette 100, such as a lighted tip 118.

The second end portion 102 of the cartridge 105 and the first end portion 115 of the battery unit 110 may include elements complementary to each other to provide for a conveniently detachable, yet secure, connection. As shown in FIG. 1, the connecting end portions of the cartridge 105 and battery unit 110 may be configured as telescoping sleeves. For example, the cartridge 105 may include a first, outer sheath 106, and the battery unit 110 may include a recessed portion as a second, inner sheath 111. Thus, the inner diameter of the first sheath 106 may be greater than the outer diameter of the second sheath 111, such that the first sheath 106 may slide over the second sheath 111. When connected, the outer surfaces of the cartridge 105 and battery unit 110 may lie flush. That is, the cartridge 105 and the battery unit 110 may have equal or approximately equal outer diameters, and the wall thickness of the first sheath 106 may be approximately the same as the difference between the outermost diameter of the battery unit 110 and the outer diameter of the second sheath 111.

The cartridge 105 and the battery unit 110 may include inner lumens (108 and 114, respectively) in communication with each other once the components are connected, to allow for the passage of air from the external environment and delivery of vapor through the electronic cigarette 100. For example, the first end portion 101 of the cartridge 105 may be in communication with a proximal outlet (e.g. via mouthpiece 103), and the second end portion 117 of the battery unit 110 may be in communication with a distal inlet (e.g., via a notch or other inlet of the lighted tip 118), each of the inlet and outlet exposed to the external environment. In some embodiments, when the cartridge 105 and the battery unit 110 are connected, the proximal outlet and the distal inlet may be the only portions of the electronic cigarette 100 exposed to the external environment.

At least a portion of the inner lumen 108 of the cartridge 105 may be defined by a first inner member 109, such that between the outer sheath 106 and the inner member 109 there may be a cavity 107. In some embodiments, both of the first inner member 109 and the first sheath 106 may extend to the end of the cartridge 105 (e.g., terminating at the same axial position along the longitudinal axis of the cartridge 105). Similarly, the inner lumen 114 of the battery unit 110 may be defined by a second inner member 113 recessed from the end of the battery unit 110. Between the second sheath 111 and the second inner member 113 there may be a space 112. Thus, the battery unit 110 may be inserted into the cartridge 105, wherein the cavity 107 of the cartridge 105 accommodates the second sheath 111, and the space 112 of the battery unit 110 accommodates the first inner member 109. In some embodiments, the first inner member 109 of the cartridge 105 may at least partially surround the second inner member 113 of the battery unit 110 when the cartridge 105 and the battery unit 110 are connected. While FIG. 1 illustrates the battery unit 110 configured for insertion into the cartridge 105, the opposite configuration is possible such that the cartridge may be inserted into the battery unit (i.e., the battery including an outer sheath, and the cartridge including an inner sheath).

To assist in securing the two components together, the telescoping elements may include a locking mechanism. In some embodiments, for example, one or more surfaces of the first and second sheaths 106, 111, and/or one or more surfaces of the first and second inner members 109, 113, may be configured to increase friction, e.g., via suitable materials or surface features. In some embodiments, the one or more surfaces of the sheaths 106, 111 and inner members 109, 113, may include a spring or deformable element to exert a force.

Figure 2:
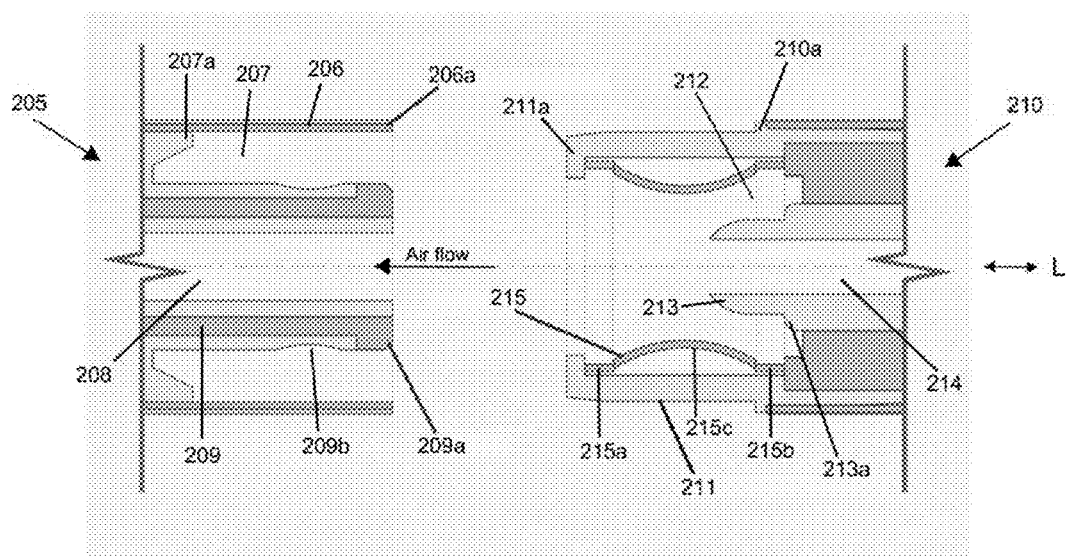
FIG. 2 shows an exemplary mechanism of a device, in accordance with one or more embodiments of the present disclosure.

FIG. 2 illustrates an exemplary locking mechanism for components 205 and 210 of an electronic vaporizing device. For example, component 205 may be a cartridge including any of the features of cartridge 105, and component 210 may be a battery unit including any of the features of battery unit 110, discussed above. Thus, cartridge 205 may include a first sheath 206, a first inner member 209, a cavity 207 defined by the first sheath 206 and first inner member 209, and an inner lumen 208. The battery unit 210 may include a second sheath 211, a second inner member 213, a space 212 defined by the second sheath 211 and the second inner member 213, and an inner lumen 214. Once the cartridge 205 and the battery unit 210 are connected, the first inner member 209 and the second inner member 213 may share a central longitudinal axis L. Further, the inner lumens 208, 214 may be in communication with each other for the passage of air from the external environment through the vaporizing device, from the battery unit 210 to the cartridge 205, as indicated in FIG. 2. In particular, the inner lumens 208, 214 may define an inner lumen of the vaporizing device, e.g., in communication with the external environment via a proximal outlet and a distal inlet. In some embodiments, the electronic vaporizing device may only be in communication with the external environment via the proximal outlet and the distal inlet.

The inside surface of the second sheath 211 may include one or more elements 215, e.g., having a first end 215a, a second end 215b, and a portion 215c therebetween that extends radially inward and is deformable such that the portion may be pushed radially outward by force. The locking mechanism may comprise, for example, a single discrete element 215, a plurality of discrete elements 215 disposed at different radial positions, and/or an annular, ring-like element 215 to completely surround the first inner member 209. In some embodiments, a plurality of elements 215 (e.g., two, three, four, five, six, seven, eight, or more elements 215) may be disposed at regular intervals along the inside surface of the second sheath 211. As shown in cross-sectional view in FIG. 2, for example, the second sheath 211 may include at least two elements 215 coupled to opposite sides of the second sheath 211, or a single annular element 215 (a cross-sectional view of both embodiments being represented by FIG. 2). In at least one embodiment, the second sheath 211 may include six elements 215 disposed at regular intervals (approximately 60 degrees apart) having gaps between adjacent elements 215. For example, the second sheath 211 may include three pairs of elements 215, each pair comprising two elements 215 opposite each other and facing each other (approximately 180 degrees apart).

As shown in FIG. 2, the second sheath 211 may include proximal and distal stepped portions to limit or prevent axial movement of the element(s) 215. For example, the stepped portions may include grooves into which the first and second ends 215a, 215b may be inserted. In some embodiments, one or more elements 215 may be fixedly attached to the second sheath 211. For example, at least one of the first end 215a and the second end 215b of the element(s) 215 may be fixedly attached to the second sheath 211, such that the element(s) 215 do not rotate or move axially with respect to the second sheath 211. While FIG. 2 shows an exemplary configuration wherein the element(s) 215 are coupled to inner surface(s) of the second sheath 211, the element(s) 215 may be coupled to outer surface(s) of the first inner member 209, e.g., for applying a force against the second sheath 211 when the cartridge 205 and the battery unit 210 are connected.

In some embodiments, the element(s) 215 may be rotatable with the respect to the second sheath 211, e.g., by moving the first and second ends 215a, 215b within the grooves of the second sheath 211. For example, a plurality of elements 215 may be interconnected, e.g., coupled together at their first ends 215a and/or second ends 215b via a linkage. All or part of the linkage may be annular in shape and concentric with the second sheath 211, such as a band, ring, or circular wire. In some embodiments, the first ends 215a and/or the second ends 215b may form part of the linkage, e.g., the first and/or second ends 215a, 215b may be integral with the linkage. The annular linkage(s) may allow the plurality of elements 215 to rotate relative to the second sheath 211 while maintaining the spacing between adjacent elements 215. Thus, in some embodiments, the element(s) 215 may not inhibit rotation of the cartridge 205 and the battery unit 210 with respect to each other when the cartridge 205 and the battery unit 210 are connected and locked together.

The element(s) 215 may comprise one or more flexible materials, e.g., allowing the middle portion 215c to flex while the first and second ends 215a, 215b are coupled to the second sheath 211. In an unstressed position (as shown in FIG. 2), the middle portion 215c of the element(s) 215 may bulge radially inward. Once the battery unit 210 is inserted into the cartridge 205, the first inner member 209 may contact the element(s) 215 and force them towards the inner wall of the second sheath 211, e.g., in a stressed position. The force between the first inner member 209 and the element(s) 215 may prevent the cartridge 205 and battery unit 210 from moving with respect to each other (e.g., inhibiting axial and/or rotational movement of the components) or becoming detached.

When the cartridge 205 and the battery unit 210 are connected, a distal end 206a of the first sheath 206 may abut a stepped portion 210a of the battery unit 210. In some embodiments, the length of the portion of the first sheath 206 that overlies the second sheath 211 may be approximately equal to the length of the second sheath 211 between its proximal-most end 221a and the stepped portion 210, e.g., such that the cartridge 205 and the battery unit 210 lie flush (e.g., the cartridge 205 and the battery unit 210 having equal or approximately equal outermost diameters). As the battery unit 210 is inserted into the cartridge 205, a distal end 209a of the first inner member 209 may engage the element(s) 215, and force the element(s) 215 radially outward towards the second sheath 211. In a final inserted position, the distal end 209a of the first inner member 209 may abut a stepped portion 213a of the second inner member 213. A proximal-most end of the second inner member 213 may be tapered (as shown in FIG. 2) to facilitate placement of the first inner member 209 into the space 212 between the second sheath 211 and the second inner member 213. The first inner member 209 may include a shallow groove or concave portion 209b where it comes into contact with the element(s) 215, e.g., to receive the element(s) 215 and further inhibit movement once the components are connected.

Further, as the battery unit 210 is inserted into the cartridge 205, a proximal-most end 211a of the second sheath 211 may enter the cavity 207 of the cartridge 205, and abut a stepped portion 207a of the cavity 207 in a final inserted position. The proximal-most end 211a of the second sheath 211 also may be tapered (as shown in FIG. 2) to facilitate placement of the second sheath 211 into the cavity 207. In some embodiments, the cavity 207 of the cartridge 205 may have a shape complementary to the shape of the second sheath 211, and/or the space 212 of the battery unit 210 may have a shape complementary to the shape of the first inner member 209, e.g., to provide for a tight fit.

Materials suitable for the element(s) 215 may include metals and metal alloys (including shape memory materials), polymers and polymer blends (including plastics), and combinations thereof, among other possible flexible materials. Materials suitable for the first and second sheaths 206, 211, and first and second inner members 209, 213, include metals and metal alloys, polymers and polymer blends (including plastics), ceramics, and combinations thereof, among other suitable materials. Any of the housing materials disclosed in U.S. Publication No. 2013/0284190 A1; U.S. Publication No. 2013/0284191 A1; U.S. Provisional Application No. 61/906,803, filed Nov. 20, 2013; and/or U.S. Provisional Application No. 61/907,002, filed Nov. 21, 2013, each of which is incorporated by reference herein, may be used according to the present disclosure.

In some embodiments, at least a portion of the first and/or second sheaths 206, 211 may be flexible. For example, in at least one embodiment, at least a portion of the second inner member 213 may be flexible to allow the second inner member 213 to flex radially inward of the first inner member 209 when the cartridge 205 and the battery unit 210 are connected (e.g., as the first inner member 209 is placed within the space 212 between the second inner member 213 and the second sheath 211). In other embodiments, the first and/or second sheaths 206, 211 may be partially or completely rigid. Further, the first sheath 206, second sheath 211, first inner member 209, and/or second inner member 213 may have portions that are flexible and portions that are rigid, e.g., to facilitate the secure connection between the cartridge 205 and the battery unit 210. For example, any of the first sheath 206, the second sheath 211, the first inner member 209, and/or the second inner member 213 may comprise a combination of materials, such as different metals or metal alloys, or one or more metals and one or more non-metals, different non-metals, etc. In at least one embodiment, the element(s) 215 may comprise a different metal than the second sheath 211 and the first inner member 209. In at least one embodiment, the first inner member 209 may comprise a combination of a metal and a non-metal. As illustrated by the lighter and darker shaded regions in FIG. 2, different portions of the cartridge 205 and battery unit 210 may comprise different materials or combinations of materials (e.g., the first inner member 209 comprising two or three different materials). Other variations and alternatives consistent with the disclosure herein will be apparent to one of ordinary skill in the art.

While the discussion herein focuses on the connection between the cartridge 105 and battery unit 110 for illustration purposes, the mechanisms presently disclosed are not limited to those particular components, and may be used in connections between any vaporization device components. For example, a cartridge detachable from a battery may allow for replacing or repair of either component, refilling the cartridge (e.g., with a suitable composition, including those disclosed in U.S. Provisional Application No. 61/826,318, filed May 22, 2013; U.S. Provisional Application No. 61/856,374, filed Jul. 19, 2013; and/or U.S. Provisional Application No. 61/969,650, filed Mar. 24, 2014; incorporated by reference herein), or recharging the battery and/or receiving data from the battery unit (e.g., including any of the methods, systems, or other features disclosed in U.S. Provisional Application No. 61/847,364, filed Jul. 17, 2013; and/or U.S. Provisional Application No. 61/971,340, filed Mar. 27, 2014; incorporated by reference herein). Detaching the cartridge 105 from the battery unit 110 also may allow for replacement or repair of any portions of those components, such as a heating coil, wick, core, reservoir, or other portion of a vaporization unit (e.g., including any of the features of a vaporization unit disclosed in U.S. Pat. No. 8,539,959; U.S. Provisional Application No. 61/906,803, filed Nov. 20, 2013; U.S. Provisional Application No. 61/938,451, filed Feb. 11, 2014; U.S. Provisional Application No. 61/907,002, filed Nov. 21, 2013; U.S. Provisional Application No. 61/970,587, filed Mar. 26, 2014; U.S. Provisional Application No. 61/968,855, filed Mar. 31, 2014; and/or U.S. Provisional Application No. 61/938,451, filed Feb. 11, 2014; incorporated by reference herein).

Further, the electronic cigarette 100 and other electronic vaporizing devices consistent with the present disclosure may include other components in addition to, or in replacement of, a cartridge 105 and battery unit 110. Further, any of the features disclosed in U.S. Publication No. 2013/0284190 A1; U.S. Publication No. 2013/0284191 A1; U.S. Provisional Application No. 61/906,803, filed Nov. 20, 2013; U.S. Provisional Application No. 61/907,002, filed Nov. 21, 2013; U.S. Pat. No. 8,539,959; U.S. Provisional Application No. 61/918,480, filed Dec. 19, 2013; U.S. Provisional Application No. 61/906,795, filed Nov. 20, 2013; U.S. Provisional Application No. 61/907,002, filed Nov. 21, 2013; U.S. Provisional Application No. 61/907,003, filed Nov. 21, 2013; U.S. Publication No. 2013/0276802 A1; and/or U.S. Provisional Application No. 61/906,803, filed Nov. 20, 2013 (e.g., regarding a housing, lighted tip, or filter), incorporated by reference herein, may be used according to the present disclosure.

Any features discussed on connection with a particular embodiment may be used in any other embodiment disclosed herein. Further, other embodiments of the present disclosure, e.g., having variations in dimensions, shapes, configurations, etc., will be apparent to those skilled in the art from consideration of the specification and practice of the embodiments disclosed herein. It is intended that the specification and examples be considered as exemplary only, with a true scope and spirit of the present disclosure being indicated by the following claims.

What is claimed is:

1. A vaporizing device comprising:
a first component;
a second component having an outermost diameter equal to an outermost diameter of the first component, the second component being connectable to, and removable from, the first component; and
at least one locking element coupled to the second component for restricting movement between the first and second components when the first and second components are connected;
wherein an end portion of the first component includes a sheath configured to slide around an end portion of the second component for connecting the first component to the second component;
wherein the end portion of the second component includes a sheath configured to slide around an inner member of the first component;
wherein the at least one locking element is coupled to an inside surface of the sheath of the second component;
wherein each of the first component and the second component defines a lumen, such that, when connected, the lumens are in communication with each other and with an external environment; and
wherein one of the first component or the second component comprises a battery unit, and the other of the first component or the second component comprises a cartridge.

2. The vaporizing device of claim 1, wherein the at least one locking element includes a surface feature of the second component, and wherein the at least one locking element is configured to apply a force radially inward.

3. The vaporizing device of claim 1, wherein the at least one locking element includes a plurality of elements coupled to the inside surface of the sheath of the second component.

4. The vaporizing device of claim 3, wherein each element of the plurality of elements comprises a middle portion configured to flex in a radial direction.

5. The vaporizing device of claim 3, wherein the plurality of elements include at least two elements coupled to inside surfaces on opposite sides of the sheath of the second component.

6. The vaporizing device of claim 1, wherein the cartridge includes a liquid.

7. The vaporizing device of claim 3, wherein the plurality of elements are rotatable with respect to the second component to which they are coupled.

8. The vaporizing device of claim 1, wherein the vaporizing device comprises a rechargeable electronic cigarette.

9. A vaporizing device comprising:
a first component;
a second component having an outermost diameter equal to an outermost diameter of the first component, the second component being connectable to, and removable from, the first component; and
at least one locking element coupled to the second component for restricting movement between the first and second components when the first and second components are connected, the at least one locking element being rotatable relative to the second component;
wherein an end portion of the first component includes a sheath configured to slide around an end portion of the second component for connecting the first component to the second component;
wherein the end portion of the second component includes a sheath configured to slide around an inner member of the first component;
wherein the at least one locking element is coupled to an inside surface of the sheath of the second component; and
wherein one of the first component or the second component comprises a battery unit, and the other of the first component or the second component comprises a cartridge.

10. The vaporizing device of claim 9, wherein each of the first component and second component defines a lumen, such that, when the first and second components are connected, the lumens are in communication with each other and with an external environment for passage of air through the vaporizing device.

11. The vaporizing device of claim 10, wherein the first component and the second component are in communication with the external environment via an inlet at a second end portion of the vaporizing device and an outlet at a first end portion of the vaporizing device.

12. The vaporizing device of claim 9, wherein a portion of the at least one locking element is annular in shape, the at least one locking element being configured to apply a force radially inward against the inner member of the first component.

13. The vaporizing device of claim 9, wherein the end portion of the second component has an outer diameter less than an outer diameter of a remainder of the second component.

14. The vaporizing device of claim 13, wherein the sheath of the first component has a wall thickness approximately equal to a difference in the outer diameter of the end portion of the second component and the remainder of the second component.

15. A vaporizing device comprising:
a first component;
a second component connectable to, and removable from, the first component; and
at least one locking element for restricting movement between first and second components when the first and second components are connected;
wherein an end portion of the first component includes a sheath configured to slide around an end portion of the second component for connecting the first component to the second component;
wherein the end portion of the second component includes a sheath configured to slide around an inner member of the first component;
wherein the at least one locking element is coupled to an inside surface of the sheath of the second component;
wherein one of the first component or the second component comprises a battery unit, and the other of the first component or the second component comprises a cartridge;
wherein the cartridge and the battery unit are rotatable relative to each other while connected and locked together via the at least one locking element; and
wherein the vaporizing device comprises an electronic cigarette.

16. The vaporizing device of claim 15, comprising an outlet at a distal end of the vaporizing device and an inlet at a proximal end of the vaporizing device for passage of air through the vaporizing device, the inlet and the outlet being in communication with each other and with the external environment.

17. The vaporizing device of claim 15, wherein the battery unit includes a rechargeable battery.

18. The vaporizing device of claim 9, wherein the at least one locking element is rotatable about a central axis of the second component.

19. The vaporizing device of claim 15, wherein the at least one locking element includes a plurality of elements coupled to the cartridge or the battery unit, the plurality of elements being interconnected and rotatable with respect to the cartridge or the battery unit to which they are coupled.

* * * * *